United States Patent [19]

Berg et al.

[11] Patent Number: 4,670,105

[45] Date of Patent: Jun. 2, 1987

[54] DEHYDRATION OF PROPANOIC ACID BY EXTRACTIVE DISTILLATION

[76] Inventors: Lloyd Berg; An-I Yeh, both of 1314 S. Third Ave., Bozeman, Mont. 59715

[21] Appl. No.: 848,980

[22] Filed: Apr. 7, 1986

[51] Int. Cl.$^4$ ............................................... B01D 3/40
[52] U.S. Cl. ...................................... 203/15; 203/51; 203/57; 203/60; 562/606
[58] Field of Search .................. 203/60, 51, 57, 15, 203/16; 562/606, 608, 609

[56] References Cited

U.S. PATENT DOCUMENTS

| | | | |
|---|---|---|---|
| 1,843,434 | 2/1932 | Wietzel et al. | 562/609 |
| 3,951,755 | 4/1976 | Sartorius et al. | 203/60 |
| 4,217,460 | 8/1980 | Hohenschutz et al. | 562/609 |
| 4,262,140 | 4/1981 | Bott et al. | 562/609 |
| 4,358,609 | 11/1982 | Hardy | 562/609 |
| 4,551,208 | 11/1985 | Bott et al. | 203/57 |
| 4,576,683 | 3/1986 | Cohen | 203/60 |

FOREIGN PATENT DOCUMENTS 156309 10/1985 European Pat. Off. ............ 562/609

Primary Examiner—Wilbur Bascomb

[57] ABSTRACT

Propanoic acid cannot be completely removed from propanoic-water mixtures by distillation because of the presence of the minimum azeotrope. Propanoic acid can be readily removed from mixtures containing it and water by using extractive distillation in which the extractive distillation agent is an acid amide. Typical examples of effective agents are acetamide; dimethylformamide and methyl glutaronitrile; formamide, adiponitrile and N,N-dimethylacetamide.

7 Claims, No Drawings

DEHYDRATION OF PROPANOIC ACID BY EXTRACTIVE DISTILLATION

FIELD OF THE INVENTION

This invention relates to a method for dehydrating propanoic acid using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compouds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the exterative agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

There are currently two commercial methods for manufacturing propanoic acid. One is the reaction of ethylene, carbon monoxide and steam under pressure. The other is to obtain the propanoic acid as a by-product from the fermentation of wood waste. Both of these processes yield an aqueous mixture of propanoic acid. However the components of this mixture cannot be separated by conventional rectification because propanoic acid boiling at 141.4° C. forms a minimum azeotrope with water boiling at 99.1° C. and containing 82.2 wt. % water. Thus it is impossible to separate completely propanoic acid from water by rectification because as soon as the minimum azeotrope composition is attained, no further change in composition will occur.

Extractive distillation would be an attractive method of effecting the separation of propanoic acid from water if agents can be found that (1) will break the propanoic acid - water azeotrope and (2) are easy to recover from propanoic acid, that is, form no azeotrope with propanoic acid and boil sufficiently above propanoic acid to make the separation by rectification possible with only a few theoretical plates.

Extractive distillation typically requires the addition of an equal amount to twice as much extractive agent as the formic acid - water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with propanic acid otherwise it will form a two-phase azeotrope with the propanoic acid in the recovery column and some other method of separation will have to be employed.

The breaking of the propanoic acid - water azeotrope is a new concept. The separation of propanoic acid from water has been investigated using activated carbon, macroreticular resins, flocculation, ozonization, anaerobic fermentation, zeolite tuff and solvent extraction with n-heptane. All of these are more effective when applied to dilute concentrations of propanoic acid.

OBJECTIVE OF THE INVENTION

The object of this invention is to provide a process or method of extractive distillation that will enhance the relative volatility of water from propanoic acid in their separation in a rectification column. It is a further object of this invention to identify suitable extractive distillation agents which will eliminate the propanoic acid - water azeotrope and make possible the production of pure propanoic acid and water by rectification. It is a further object of this invention to identify organic compounds which in addition to the above constraints, are stable, can be separated from propanoic acid by rectification with relatively few theoretical plates and can be recycled to the extractive distillation column and re-used with little decomposition.

SUMMARY OF THE INVENTION

The objects of the invention are provided by a process for separating propanoic acid from water which entails the use of acid amides, either alone or admixed with certain oxgenated, nitrogenous and/or sulfur containing organic compounds.

DETAILED DESCRIPTION OF THE INVENTION

We have discovered that acid amides, either alone or admixed with other organic compounds, will effectively negate the propanoic acid - water minimum azeotrope and permit the separation of pure water from propanoic acid by rectification when employed as the agent in extractive distillation. Table 1 lists several acid amides and their mixtures and the approximate proportions that we have found to be effective. The data in Table 1 was obtained in a vapor-liquid equilbrium still. In each case, the starting material was the propanoic acid - water azeotrope. The ratios are the parts by weight of extractive agent used per part of propanoic acid - water azeotrope. The relative volatilities are listed for each of the two ratios employed. The compounds which are effective when used alone are dimethylformamide, acetamide and N,N-dimethylacetamide.

The compounds which are effective when used in mixtures with acid amides are formamide, adiponitrile, dimethylsulfoxide and methyl glutaronitrile. The two relative volatilities shown in Table 1 correspond to the two different ratios employed. For example, in Table 1, one part of dimethylformamide (DMFA) with one part of the propanoic acid - water azeotrope gives a relative volatility of 9.0, 6/5 parts of DMFA give 25.0. One half part of acetamide mixed with one half part of formamide with one part of the propanoic acid - water azeotrope gives a relative volatility of 9.0, 3/5 parts of acetamide plus 3/5 parts of formamide give 7.5. One third part of N,N-dimethylacetamide plus ⅓ part of formamide plus ⅓ part of adiponitrile with one part of the propanoic acid - water azeotrope gives a relative volatility of 14.7, with 2/5 parts, these three give a relative volatility of 13.8. In every example in Table 1, the starting material is the propanoic acid - water azeotrope which possesses a relative volatility of 1.00.

composition was 1.8% water, 98.2% propanoic acid which is a relative volatility of 8.8. After 1.5 hours of steady operation, samples were again taken. The overhead composition was 99.8% water, 0.2% propanoic acid, the bottoms composition was 2% water, 98% propanoic acid which is a relative volatility of 9.4. This indicates that the minimum azeotrope has been negated and separation accomplished. Without the extractive agent, the overhead would have approached the the minimum azeotrope composition of 82.2% water. This proves that the extractive agent is negating the azeotrope and makes the rectification proceed as if the azeotrope no longer existed and brings the more volatile component, water, out as overhead. It is our belief that this is the first time this has been accomplished for this azeotrope.

THE USEFULNESS OF THE INVENTION

The usefulness or utility of this invention can be dem-

TABLE 1

Effective Extractive Distillation Agents.

| Compounds | Ratios | | Relative Volatilities | |
|---|---|---|---|---|
| Dimethylformamide (DMFA) | 1 | 6/5 | 9.0 | 25.0 |
| DMFA, Acetamide | $(1/2)^2$ | $(3/5)^2$ | 5.2 | 5.8 |
| DMFA, Adiponitrile | $(1/2)^2$ | $(3/5)^2$ | 11.9 | 9.1 |
| DMFA, N,N—Dimethylacetamide | $(1/2)^2$ | $(3/5)^2$ | 12.2 | 10.0 |
| DMFA, Dimethylsulfoxide | $(1/2)^2$ | $(3/5)^2$ | 13.6 | 13.8 |
| DMFA, Methyl glutaronitrile | $(1/2)^2$ | $(3/5)^2$ | 13.7 | 16.9 |
| DMFA, Acetamide, Formamide | $(1/3)^3$ | $(2/5)^3$ | 11.4 | 4.9 |
| DMFA, Acetamide, N,N—Dimethylacetamide | $(1/3)^3$ | $(2/5)^3$ | 2.2 | 3.9 |
| DMFA, Acetamide, Dimethylsulfoxide | $(1/3)^3$ | $(2/5)^3$ | 5.5 | 4.1 |
| DMFA, N,N—Dimethylacetamide, Adiponitrile | $(1/3)^3$ | $(2/5)^3$ | 27.5 | 24.0 |
| DMFA, N,N—Dimethylacetamide, Formamide | $(1/3)^3$ | $(2/5)^3$ | 20.0 | 17.2 |
| DMFA, N,N—Dimethylacetamide, Dimethylsulfoxide | $(1/3)^3$ | — | 12.5 | — |
| DMFA, N,N—Dimethylacetamide, Methyl glutaronitrile | $(1/3)^3$ | — | 20.4 | 8.4 |
| Acetamide | 1 | 6/5 | 9.0 | 11.2 |
| Acetamide, Formamide | $(1/2)^2$ | $(3/5)^2$ | 9.0 | 7.5 |
| N,N—Dimethylacetamide | 1 | 6/5 | 20.0 | 14.0 |
| N,N—Dimethylacetamide, Acetamide | $(1/2)^2$ | $(3/5)^2$ | 5.5 | 3.4 |
| N,N—Dimethylacetamide, Adiponitrile | $(1/2)^2$ | $(3/5)^2$ | 15.1 | 19.5 |
| N,N—Dimethylacetamide, Formamide | $(1/2)^2$ | $(3/5)^2$ | 16.2 | 10.7 |
| N,N—Dimethylacetamide, Formamide, Acetamide | $(1/3)^3$ | $(2/5)^3$ | 6.0 | 9.8 |
| N,N—Dimethylacetamide, Formamide, Adiponitrile | $(1/3)^3$ | $(2/5)^3$ | 14.7 | 13.8 |
| N,N—Dimethylacetamide, Formamide, Methyl glutaronitrile | $(1/3)^3$ | $(2/5)^3$ | 23.0 | 12.5 |
| Formamide, Adiponitrile | $(1/2)^2$ | $(3/5)^2$ | 10.5 | 10.1 |
| Formamide, Methyl glutaronitrile | $(1/2)^2$ | $(3/5)^2$ | 13.4 | 7.4 |

TABLE 2

Data From Run Made In Rectification Column.

| | | Wt. % - 1 hr. | Wt. % - 1.5 hrs. |
|---|---|---|---|
| Overhead: | Water | 99.7 | 99.8 |
| | Propanoic acid | 0.3 | 0.2 |
| Bottoms: | Water | 1.8 | 2.0 |
| | Propanoic acid | 98.2 | 98.0 |
| Relative Volatility | | 8.8 | 9.4 |

One of the compounds, DMFA, listed in Table 1 and whose relative volatility had been determined in the vapor-liquid equilibrium still, was then evaluated in a glass perforated plate rectification column possessing 4.5 theoretical plates and the results listed in Table 2. The data in Table 2 was obtained in the following manner. The charge was 95 wt. % propanoic acid and 5 wt. % water and after a half hour of operation in the 4.5 theoretical plate column to establish equilibrium, DMFA at 50° C. and 20 ml/min. was pumped in. The rectification was continued with sampling of overhead and bottoms after one hour and 1.5 hours. After one hour of steady operation, the overhead composition was 99.5% water, 0.5% propanoic acid and the bottoms onstrated by referring to the data presented in Tables 1 and 2. All of the successful extractive distillation agents show that propanoic acid an water can be separated from their mimimum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small.

WORKING EXAMPLES.

Example 1

Fifty grams of the propanoic acid - water azeotrope and fifty grams of acetamide were charged to an Othmer type glass vapor-liquid equilbrium still and refluxed for 15 hours. Analysis of the vapor and liquid by gas chromatography gave vapor composition of 97.6% water, 2.4% propanoic acid and a liquid composition of 82.2% water, 17.8% propanoic acid. This indicates a relative volatility of 9.0. Ten grams of acetamide were added and refluxing continued for another 13 hours. Analysis indicated a vapor composition of 98.2% water, 1.8% propanoic acid; a liquid composition of 83.3% water, 16.7% propanoic acid which is a relative volatility of 11.2.

Example 2

Fifty grams of the propanoic acid - water azeotrope, 25 grams of DMFA and 25 grams of methyl glutaronitrile were charged to the vapor-liquid equilibrium still and refluxed for eleven hours. Analysis indicated a vapor composition of 97.2% water, 2.8% propanoic acid, a liquid composition of 71.9% water, 28.1% propanoic acid which is a relative volatility of 13.7. Five grams of DMFA and five grams of emthylglutaronitrile were added and refluxing continued for another nine hours. Analysis indicated a vapor composition of 97.6% water, 2.4% propanoic acid, a liquid composition of 70.5% water, 29.5% propanoic acid which is a relative volatility of 16.9.

Example 3

Fifty grams of the propanoic acid- water azeotrope, 17 grams of formamide, 17 grams of adiponitrile and 17 grams of N,N-dimethylacetamide were charged to the vapor-liquid equilibrium still and refluxed for 14 hours. Analysis indicated a vapor composition of 98.8% water, 1.2% propanoic acid; a liquid composition of 84.6% water, 15.4% propanoic acid which is a relative volatility of 14.7. Three grams each of formamide, adiponitrile and N,N-dimethylacetamide were added and refluxing continued for another ten hours. Analysis indicated a vapor composition of 98.8% water, 1.2% propanoic acid; a liquid composition of 85.7% water, 14.3% propanoic acid which is a relative volatility of 13.8.

Example 4

A glass perforated plate rectification column was calibrated with ethylbenzene and p-xylene which possesses a relative volatility of 1.06 and found to have 4.5 theoretical plates. A solution comprising 380 grams of propanoic acid and 20 grams of water was placed in the stillpot and heated. When refluxing began, an extractive agent consisting of dimethylformamide (DMFA) was pumped into the column at a rate of 20 ml/min. The temperature of the extractive agent as it entered the column was 50° C. After establishing the feed rate of the extractive agent, the heat input to the propanoic acid and water in the stillpot was adjusted to give a total reflux rate of 10–20 ml/min. After one hour of operation, the overhead and bottoms samples of approximately two ml. were collected and analysed using gas chromatography. The overhead analysis was 99.7% water, 0.3% propanoic acid. The bottoms analysis was 1.8% water, 98.2% propanoic acid. Using these compositions in the Fenske equation, with the number of theoretical plates in the column being 4.5, gave an average relative volatility of 8.8 for each theoretical plate. After 1½ hours of total operating time, the overhead and bottoms samples were again taken and analysed. The overhead composition was 99.8% water, 0.2% propanoic acid and the bottoms composition was 2% water, 98% propanoic acid. This gave an average relative volatility of 9.4 for each theoretical plate.

We claim:

1. A method for recovering propanoic acid from a mixture of propanoic acid and water which comprises distilling a mixture of propanoic acid and water in a rectification column in the presence of about one part of extractive agent per part of propanoic acid - water mixture, recovering the water as overhead product and obtaining the propanoic acid and extractive agent from the stillpot, the extractive agent comprises acetamide.

2. The method of claim 1 in which the extractive agent comprises a mixture of acetamide and formamide.

3. A method for recovering propanoic acid from a mixture of propanoic acid and water which comprises distilling a mixture of propanoic acid and water in a rectification column in the presence of about one part of extractive agent per part of propanoic acid - water mixture, recovering the water as overhead product and obtaining the propanoic acid and extractive agent from the stillpot, the extractive agent comprises dimethylformamide.

4. The method of claim 3 in which the extractive agent comprises a mixture of dimethylformamide and at least one material from the group consisting of adiponitrile, methyl glutaronitrile, acetamide, N,N-dimethylacetamide, dimethylsulfoxide and formamide.

5. A method for recovering propanoic acid from a mixture of propanoic acid and water which comprises distilling a mixture of propanoic acid and water in a rectification column in the presence of about one part of extractive agent per part of propanoic acid - water mixture, recovering the water as overhead product and obtaining the propanoic acid and extractive agent from the stillpot, the extractive agent comprises N,N-dimethylacetamide.

6. The method of claim 5 in which the extractive agent comprises a mixture of N,N-dimethylacetamide and at least one material from the group consisting of acetamide, formamide, and methyl glutaronitrile.

7. A method for recovering propanoic acid from a mixture of propanoic acid and water which comprises distilling a mixture of propanoic acid and water in a rectification column in the presence of about one part of extractive agent per part of propanoic acid - water mixture, recovering the water as overhead product and obtaining the propanoic acid and extractive agent from the stillpot, the extractive agent comprises a mixture of formamide and at least one material from the group consisting of adiponitrile and methyl glutaronitrile.

* * * * *